(12) United States Patent
Lin et al.

(10) Patent No.: US 10,902,936 B2
(45) Date of Patent: Jan. 26, 2021

(54) TRACKING INFECTIONS IN HOSPITAL ENVIRONMENTS

(71) Applicant: KONINKLIJKE PHILIPS N.V., Eindhoven (NL)

(72) Inventors: Henry Lin, Quincy, MA (US); Sitharthan Kamalakaran, Pelham, NY (US)

(73) Assignee: Koninklijke Philips N.V., Eindhoven (NL)

( * ) Notice: Subject to any disclaimer, the term of this patent is extended or adjusted under 35 U.S.C. 154(b) by 392 days.

(21) Appl. No.: 15/742,929

(22) PCT Filed: Jul. 11, 2016

(86) PCT No.: PCT/IB2016/054139
§ 371 (c)(1),
(2) Date: Jan. 9, 2018

(87) PCT Pub. No.: WO2017/009770
PCT Pub. Date: Jan. 19, 2017

(65) Prior Publication Data
US 2019/0087535 A1 Mar. 21, 2019

Related U.S. Application Data

(60) Provisional application No. 62/191,684, filed on Jul. 13, 2015.

(51) Int. Cl.
*G16B 20/00* (2019.01)
*G16B 10/00* (2019.01)
*G16H 50/30* (2018.01)

(52) U.S. Cl.
CPC ............ *G16B 20/00* (2019.02); *G16B 10/00* (2019.02); *G16H 50/30* (2018.01)

(58) Field of Classification Search
CPC ................................ G16B 20/00; G16B 10/00
USPC ........................................................ 702/20
See application file for complete search history.

(56) References Cited

U.S. PATENT DOCUMENTS

2008/0206767 A1    8/2008   Kreiswirth et al.

FOREIGN PATENT DOCUMENTS

WO    2014146096 A1    9/2014

OTHER PUBLICATIONS

D. Huson, "Phylogeny", Grundlagen der Bioinformatik, May 18, 2009; retrieved from the Internet: URL:https://ab.inf.uni-tuebingen.de/teaching/ss09/gbi/scri pt/05-phylogeny.pdf (Abstract).

*Primary Examiner* — Jerry Lin

(57) ABSTRACT

The present invention provides for a method to identify a hospital acquired infection. The method includes computing the number of changes over time between an infection sample and at least a subset of the plurality of infection samples and determining if the number of changes over time is within an interval of an expected number of changes. If so, marking the infection sample as a hospital acquired infection.

14 Claims, 3 Drawing Sheets

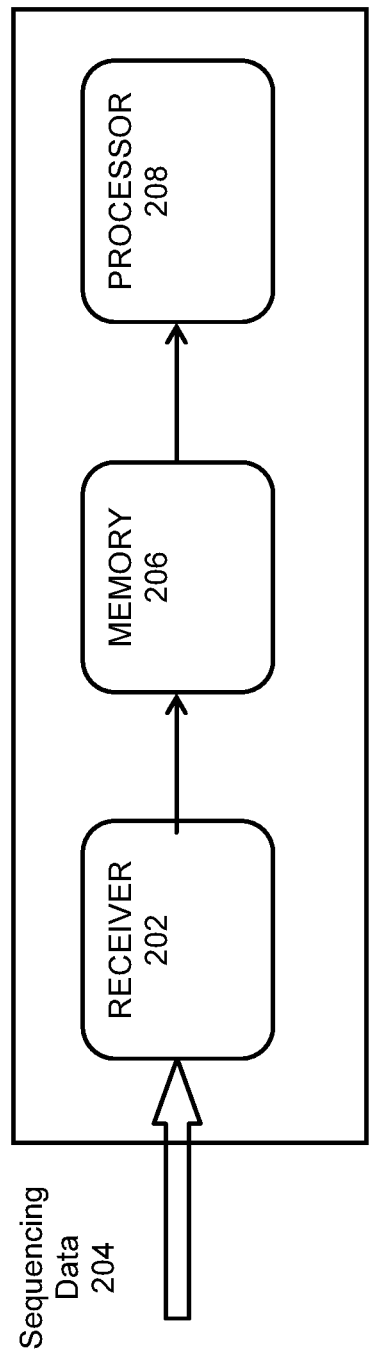

TRACKING INFECTIONS IN HOSPITAL ENVIRONMENTS

CROSS-REFERENCE TO PRIOR APPLICATIONS

This application is the U.S. National Phase application under 35 U.S.C. § 371 of International Application No. PCT/M2016/054139, filed on Jul. 11, 2016, which claims the benefit of Provisional Application Ser. No. 62/191,684, filed Jul. 13, 2015. These applications are hereby incorporated by reference herein, for all purposes.

FIELD

Various embodiments described herein relate to healthcare associated infections, and more specifically, but not exclusively, to methods and apparatus for tracking the spread of hospital acquired infections.

BACKGROUND

Healthcare-associated infections (HAIs) are infections acquired by a patient during healthcare treatments for another condition. HAIs in the medical literature are often referred to as nosocomial infections. HAIs can be deadly and are a frequent occurrence in hospitals. They often have bacterial or fungal causes. Approximately 1 out of every 20 patients hospitalized will contract an HAI. The last study conducted in 2002 estimated that there were approximately 1.7 million HAIs. These 1.7 million HAIs have caused or contributed to approximately 99,000 deaths each year. A similar trend has been identified in Europe where HAI infections appear to contribute to two-thirds of the 25,000 yearly deaths.

Nosocomial infections can cause severe pneumonia and infections of the urinary tract, bloodstream and other parts of the body. Many types are difficult to treat with antibiotics, and antibiotic resistance is spreading to Gram-negative bacteria that can infect people outside the hospital context. In the United States, the most frequent type of infection hospital-wide is urinary tract infection (36%), followed by surgical site infection (20%), and bloodstream infection and pneumonia (both 11%).

The significant economic consequences of HAIs were identified in 1992 based on the Study on the Efficacy of Nosocomial Infection Control (SENIC), a study conducted in the mid-1970s. At the time of publication, the direct cost on healthcare was estimated at $6.65 billion (adjusted for inflation using CPI in 2007). However, recent published evidence estimates direct costs today between $28.4 and $33.8 billion dollars. Much of that cost is related to longer patient stays, quarantining parts of the hospital, and discovering and eradicating the source of infection.

SUMMARY

According to the foregoing, it would be desirable to provide a method and apparatus for the identification and tracking of HAIs to facilitate their control and eradication.

It is to be understood that the phraseology and terminology employed herein are for the purpose of description and not of limitation.

Various embodiments disclosed herein generally relate to healthcare associated infections, and more specifically, to methods, apparatus, and non-transitory machine-readable media storing instructions for execution by a processor for tracking the spread of hospital acquired infections in the hospital environment. To this end, some embodiments track hospital-associated infections acquired from bacterial and fungi and compare them to other samples in an evolutionary manner to help with the sourcing of transmission, identifying related cases, etc.

Various embodiments further identify infection samples that may be spreading in a single outbreak (rather than separate unrelated infections) for the purposes of aiding infection control procedures. If there are multiple patients with the same type of infection, it is important to identify which infections may have been spread within the hospital versus community acquired infections (i.e., infections transmitted outside the hospital environment).

In general, methods and systems to track the spread of an infection are disclosed. More generally, sequencing data from a sample of an infection is used to determine the main pathogen (e.g., bacterial, virus, or fungi) present. The sequencing reads are then mapped to a reference sequence of the pathogen to obtain a list of variants (such as SNPs and indels). With a collection of sequenced samples, the pairwise distances between each sample are calculated to create a distance matrix. This distance matrix is used to build a phylogenic tree of samples to show how infection outbreaks may have spread. In order to determine which infections may be related, measurements of how the pathogen may have evolved in the past are used to determine the expected rate of change over time, which are expected to be seen in the case of patient-to-patient transmission.

The expected rate of change can be calculated by using linear regression on sample data, which contains the number of changes seen over time for different samples. A prediction interval, which is an interval bounding the expected number of changes expected to be seen when an HAI is transmitted, is also calculated. Using the prediction interval at a particular threshold, such as 95%, the closely related samples can be classified as either transmitted between patients or unrelated. After determining the pairs of samples which may be related, those samples can be visually marked on the phylogenic tree by various methods, such as placing a box around related samples. These samples should typically fall within a subtree of the phylogenic tree.

Various embodiments disclosed herein include a method to track the spread of infection. The method includes building a phylogeny of infection sequenced samples based on infection sample sequencing data to identify closely-related samples; determining an expected range of changes over time for a pathogenic organism; for at least one infection sample, computing the number of mutational changes over time between that sample and at least one additional sample; for each of the computed number of mutational changes over time, determining if the number of mutational changes over time between samples is within the expected range of changes; and, for each of the computed number of mutational changes over time that are within the expected range of changes, marking the associated pair of samples as a potential transmission.

In some embodiments, the method to track the spread of infection as set out above is disclosed wherein the expected range of changes is determined by computing, for at least one of the plurality of infection samples, the number of changes over time between the sample and at least one closely-related sample as determined by the phylogeny.

In various embodiments, the method to track the spread of infection as set out above is disclosed wherein the expected range of changes is determined from a plurality of samples taken from the same patient over time or from two patients between which there was a likely transmission.

In various embodiments, the method to track the spread of infection as set out above is disclosed wherein building the phylogeny comprises computing pairwise distances between each pair of sequenced samples and using a distance matrix to build a phylogenic tree with approaches such as, e.g., FastTree2 or the Kimura 2-parameter model.

In various embodiments, the method to track the spread of infection as set out above is disclosed wherein determining an expected range of changes over time for a pathogenic organism includes using linear regression on sample data which contains changes over time for different samples and computing a prediction interval.

In various embodiments, the method to track the spread of infection as set out above is disclosed wherein the infection sample sequencing data is obtained through full genome sequencing or targeted sequencing.

In various embodiments, the method to track the spread of infection as set out above is disclosed wherein the computed number of mutational changes between samples is normalized by dividing by the total number of genomic positions for which both samples have a base call.

In various embodiments n, the method to track the spread of infection as set out above further includes determining which infection samples are from the same outbreak by conducting a breadth first search on the phylogenetic tree of the samples traversing edges with a number of changes within the expected range of changes.

In various embodiments, the method to track the spread of infection as set out above further includes marking the pairs of infection samples identified as being a potential transmission on a displayed phylogenic tree of sequenced infection samples.

In various embodiments, the method to track the spread of infection as set out above further includes creating a plurality of phylogenic trees, with each tree constructed from samples marked as being from the same outbreak.

Various embodiments relate to a system for tracking the spread of infection. The system includes a receiver for receiving infection sample sequencing data, a memory configured to store the received infection sample sequencing data, and a processor configured to: build a phylogeny of sequenced samples to identify closely-related samples; determine an expected range of changes over time for a pathogenic organism; for at least one infection sample, compute the number of mutational changes over time between that sample and at least one additional infection sample; for each of the computed number of mutational changes over time, determine if the number of mutational changes over time between samples is within the expected range of changes; and for each of the computed number of mutational changes over time that are within the expected range of changes, mark the associated pair of samples as a potential transmission.

In various embodiments, the system to track the spread of infection as set out above is disclosed wherein the configured processor determines the expected range of changes by computing, for at least one of the plurality of infection samples, the number of changes over time between the sample and at least one closely-related sample as determined by the phylogeny.

In various embodiments, the system to track the spread of infection as set out above is disclosed wherein the configured processor determines the expected range of changes from a plurality of samples taken from the same patient over time, or from two patients between which there was a likely transmission.

In various embodiments, the system to track the spread of infection as set out above is disclosed wherein the configured processor builds the phylogeny by computing pairwise distances between each pair of sequenced samples and using a distance matrix to build a phylogenic tree.

In various embodiments, the system to track the spread of infection as set out above is disclosed wherein the configured processor determines an expected range of changes over time for a pathogenic organism using linear regression on sample data which contains changes over time for different samples and computing a prediction interval.

In various embodiments, the system to track the spread of infection as set out above is disclosed wherein the infection sample sequencing data is received from a source of full genome sequencing data or targeted sequencing data.

In various embodiments, the system to track the spread of infection as set out above is disclosed wherein computed number of mutational changes between samples is normalized by dividing the total number of genomic positions for which both samples have a base call.

In various embodiments, the system to track the spread of infection as set out above is disclosed wherein the processor is further configured to determine which of the infection samples are from the same outbreak by conducting a breadth first search on the phylogenetic tree of the samples traversing edges with a number of changes within the expected range of changes.

In various embodiments, the system to track the spread of infection as set out above is disclosed wherein the processor is further configured to mark the pairs of infection samples identified as being a potential transmission on a displayed phylogenic tree of sequenced infection samples.

In various embodiments, the system to track the spread of infection as set out above is disclosed wherein the processor is further configured to create a plurality of phylogenic trees, with each tree constructed from samples marked as being from the same outbreak.

Upon reading the above description, various alternative embodiments will become apparent to those skilled in the art. These embodiments are to be considered within the scope and spirit of the subject present disclosure.

BRIEF DESCRIPTION OF THE DRAWINGS

In the drawings, like reference characters generally refer to the same parts throughout the different views. In the following description, various embodiments are described with reference to the following drawings, in which:

FIG. 2 is a schematic representation of an embodiment of a system to track an infection.

DETAILED DESCRIPTION

The description and drawings presented herein illustrate various principles. It will be appreciated that those skilled in the art will be able to devise various arrangements that, although not explicitly described or shown herein, embody these principles and are included within the scope of this disclosure. As used herein, the term, "or," as used herein, refers to a non-exclusive or (i.e., and/or), unless otherwise indicated (e.g., "or else" or "or in the alternative"). Additionally, the various embodiments described herein are not necessarily mutually exclusive and may be combined to produce additional embodiments that incorporate the principles described herein.

The present disclosure of various embodiments satisfies the needs discussed above. Embodiments generally relate to healthcare associated infections, and more specifically, to methods and apparatus for the tracking of hospital acquired infections.

Figure 1A:
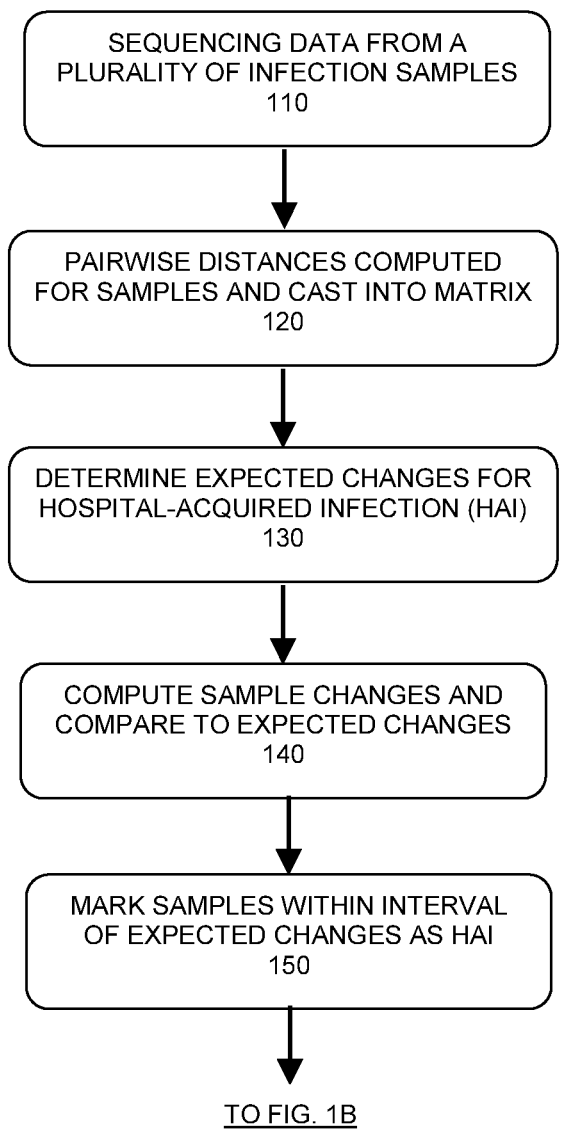
FIG. 1A-B is a schematic representation of an embodiment of a method to track an infection.
Figure 1B:
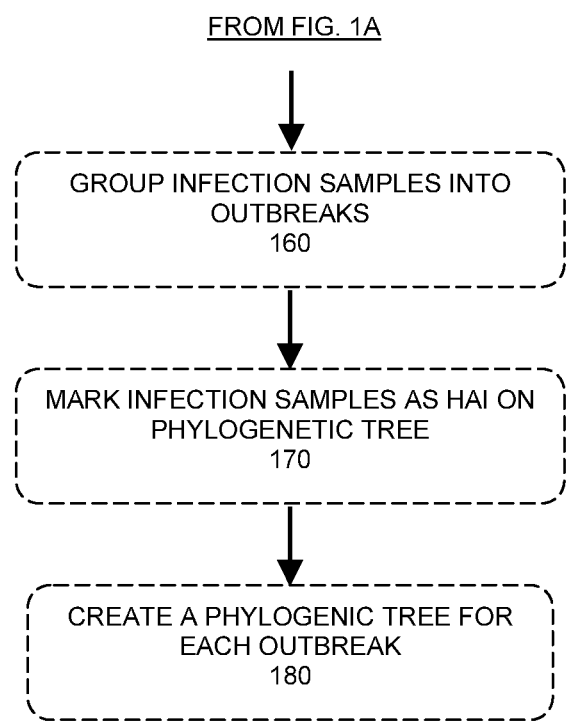

Referring to FIG. 1, a schematic representation 100 of a method to track a hospital acquired infection in accordance with various embodiments is illustrated. In step 110, each infection sample in a plurality of infection samples is sequenced. The sequencing can be performed using various sequencing technologies, e.g., next-generation sequencing technology such as Illumina HiSeq or MiSeq, or Pacific Biosciences. Embodiments can utilize data from full genome sequencing or targeted sequencing of the organism.

The sequencing data is processed and compared to one or more reference sequences for the sequenced organism. The appropriate reference sequence can be identified using, e.g., prior knowledge or MLST typing. Once the reference sequence is chosen, the sequenced data can be aligned to the reference sequence using well-known methods such as BWA, Bowtie, etc., and differences between the sequenced data and the reference sequence can be identified by various methods to call variants, such as samtools or GATK. Variations in the genome may be annotated to determine which mutations occur within important genes or in less important regions of the genome.

In step 120, the pairwise distances between each pair of sequenced samples is calculated using, e.g., the R statistical modeling language and an R package such as APE, available at http://cran.r-project.org/web/packages/ape/index.html, and used to form a distance matrix. The distance matrix can be based on the absolute number of differences or based on a probabilistic model, such as Jukes-Cantor. This distance matrix may then be used for building a phylogenic tree of sequenced samples and identifying any closely-related samples for each of the sequenced samples.

In step 130, an expected range of changes over time for a transmitted infection is determined. One procedure for determining the expected range of changes over time involves examining neighbors that the phylogenic tree indicates are closely related, i.e., those neighbors which only have a limited number of changes between them (e.g. 10 SNPs) and are believed to be evolutionarily related, and measuring the range of changes between their genomes and dividing by the time between the isolation of their originating infections. Linear regression may also be used on the sample data to determine the average range of changes per unit time. Alternative procedures for determining the expected range of changes over time could include utilizing a controlled method, such as taking samples from the same patient over known period(s) of time and measuring the observed changes, using previously-determined information from third party sources or publications, or determining the expected range of changes from a plurality of samples taken from a known hospital-acquired infection. Other methods can be used to compute prediction intervals on the range of changes expected to be seen over time, and these intervals can be used to bound the typical range of expected changes.

In step 140, for at least one infection sample, the number of mutational changes over time between that sample and at least one additional infection sample is computed, and it is determined if the number of changes over time between those sample pairs is within or without an interval of the expected range of changes.

For example, the pairwise distances between each pair of samples may be computed based on the number of SNP differences between the samples. The number of mutational changes may also be determined by counting, e.g., indels (insertions and deletions), genomic rearrangements (inversions and translocations), copy number changes, the absence or presence of genes, or some combination of the preceding features, and these changes may be measured in the full genome of an organism or part of the genome, such as the organism's chromosomes or plasmid.

Once the pairwise distances have been calculated, each sample may be compared with every other sample to determine if the number of differences between the pair of samples falls within the expected range of differences we would expect to see from a transmitted infection given the time difference between the samples. The computed number of mutational changes between the samples may be normalized using the total number of genomic positions for which both samples have a base call, thereby reducing errors and noise arising in the physical transduction in the sample sequencing process.

In step 150, for each pair of samples where the computed number of changes over time is within an interval of the expected range of changes, the associated pair of samples are marked as a potentially-transmitted infection. For example, if the number of changes is within some prediction interval, e.g., 95%, of the number of changes that are expected based on previous data, the sample would be marked as a potentially-transmitted infection.

In various embodiments, a method to identify a transmitted infection as set out above is disclosed along with the step 160 of determining which of the infection samples are from the same outbreak. This can be accomplished by conducting a breadth first search on a graph where each patient is a node and there is an edge between two nodes if the foregoing steps determine there likely was a transmission between the patients. Such a search essentially identifies patients within the same outbreak by starting with one patient and noting the other patients that have been marked as likely having received an infection from that patient. The process iterates by identifying the patients that have likely in turn received an infection from those patients that received an infection from the original patient and so on until no new patients are identified.

In various embodiments, a method to identify a transmitted infection as set out above is disclosed along with the step 170 of marking the infection samples identified as being transmitted infections on a phylogenic tree of sequenced infection samples. The phylogenic tree may be the original phylogenic tree computed in connection with the transmission determination above or it may be a recomputed phylogenic tree that accounts for transmitted infections as discussed above. The actual display of transmitted infections may be, e.g. the highlighting of a cluster or subtree of samples on the displayed tree.

In various embodiments, a method to identify a transmitted infection as set out above is disclosed along with the step 180 of creating a plurality of phylogenic trees, with each tree associated with a separate outbreak.

Referring to FIG. 2, a schematic representation 200 of a system to identify a transmitted infection in accordance with various embodiments is illustrated. The system 200 includes a receiver 202 for receiving infection sample sequencing data 204, a memory 206 configured to store the received infection sample sequencing data 204 and a processor 208.

Processor 208 is configured as discussed above to build a phylogeny of sequenced samples to identify any closely-related samples for each of the sequenced samples; determine an expected range of changes over time for a transmitted infection; for each of the plurality of infection samples, compute the number of changes over time between that sample and at least one other infection sample; for each of the computed number of changes over time, determine if the number of changes over time is within an interval of the expected range of changes; and for each of the computed number of changes over time that are within the interval of the expected range of changes, marking the associated pair of samples as a transmitted infection.

The processor 208 may include one or more microprocessors, field-programmable gate arrays (FPGAs), application-specific integrated circuits (ASICs), other similar devices, or combinations thereof. The memory 206 may include various memory devices such as cache (L1/L2/L3 cache), system memory, or storage. As used herein, the term "non-transitory machine-readable medium" will be understood to encompass both volatile (e.g., DRAM and SRAM) and non-volatile (e.g., flash, magnetic, and optical) memories, but to exclude transitory signals.

In various embodiments, a system to identify a transmitted infection as set out above is disclosed wherein the configured processor determines the expected range of changes by computing, for at least one of the plurality of infection samples, the number of changes over time between the sample and at least one closely-related sample as determined by the phylogeny.

In various embodiments, a system to identify a transmitted infection as set out above is disclosed wherein the configured processor determines the expected range of changes from a plurality of samples taken from the same patient over time, or from two patients between which there was a likely transmission.

In various embodiments, a system to identify a transmitted infection as set out above is disclosed wherein the configured processor builds the phylogeny by computing pairwise distances between each pair of sequenced samples and using a distance matrix to build a phylogenic tree.

In various embodiments, a system to identify a transmitted infection as set out above is disclosed wherein the configured processor determines an expected range of changes over time for a pathogenic organism by using linear regression on sample data which contains changes over time for different samples and computing a prediction interval.

In various embodiments, a system to identify a transmitted infection as set out above is disclosed wherein the infection sample sequencing data is received from a source of full genome sequencing data or targeted sequencing data.

In various embodiments, a system to identify a transmitted infection as set out above is disclosed wherein the computed number of mutational changes between samples is normalized by dividing by the total number of genomic positions for which both samples have a base call.

In various embodiments, a system to identify a transmitted infection as set out above is disclosed wherein the processor is further configured to determine which of said infection samples are from the same outbreak by conducting a breadth first search on the phylogenetic tree of the samples traversing edges with a number of changes within the expected range of changes.

In various embodiments, a system to identify a transmitted infection as set out above is disclosed wherein the processor is further configured to mark the pairs of infection samples identified as being a potential transmission on a displayed phylogenic tree of sequenced infection samples.

In various embodiments, a system to identify a transmitted infection as set out above is disclosed wherein the processor is further configured to create a plurality of phylogenic trees, with each tree constructed from samples marked as being from the same outbreak.

While the embodiments has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification.

What is claimed is:

1. A method to track the spread of infection, said method comprising:
    obtaining, for each of a plurality of infection samples, sequencing data;
    determining an expected range of changes over time for a pathogenic organism;
    for at least one infection sample from the plurality of infection samples, computing the number of mutational changes over time between that infection sample and at least one additional infection sample from the plurality of infection samples;
    for each of the computed number of mutational changes over time, determining if the number of mutational changes over time between the at least one infection sample and the at least one additional infection sample is within the expected range of changes;
    for each of the computed number of mutational changes over time that are within the expected range of changes, identifying the associated pair of samples as a potential transmission; and
    displaying, on a user interface, the pair of infection samples identified as being a potential transmission within a phylogenic tree of sequenced infection samples.

2. The method of claim 1, wherein the expected range of changes is determined by,
    building a phylogeny of sequenced samples to identify closely-related samples; and
    computing, for at least one of the plurality of infection samples, the number of changes over time between the sample and at least one closely-related sample as determined by the phylogeny.

3. The method of claim 1, wherein the expected range of changes is determined from a plurality of samples taken from the same patient over time or from two patients between which there was a likely transmission.

4. The method of claim 2, wherein building the phylogeny comprises computing pairwise distances between each pair of sequenced samples and using a distance matrix to build a phylogenic tree.

5. The method of claim 1, wherein determining an expected rate of changes over time for a pathogenic organism comprises using linear regression on sample data which contains changes over time for different samples and computing a prediction interval.

6. The method of claim 1, wherein the infection sample sequencing data is obtained through full genome sequencing or targeted sequencing.

7. The method of claim 1, wherein the computed number of mutational changes between samples is normalized by dividing by the total number of genomic positions for which both samples have a base call.

8. The method of claim 4 further comprising:
determining which of said infection samples are from the same outbreak by conducting a breadth first search on the phylogenetic tree of the samples traversing edges with a number of changes within the expected range of changes.

9. The method of claim 1, further comprising:
creating a plurality of phylogenic trees, with each tree constructed from samples marked as being from the same outbreak.

10. A system for tracking the spread of infection, said system comprising:
a receiver for receiving infection sample sequencing data for a plurality of infection samples;
a memory configured to store the received infection sample sequencing data; and
a processor configured to:
determine an expected range of changes over time for a pathogenic organism;
for at least one infection sample from the plurality of infection samples, compute the number of mutational changes over time between that infection sample and at least one additional infection sample from the plurality of infection samples;
for each of the computed number of mutational changes over time, determine if the number of mutational changes over time between the at least one infection sample and the at least one additional infection sample is within the expected range of changes;
for each of the computed number of mutational changes over time that are within the expected range of changes, identify the associated pair of samples as a potential transmission; and
display, on a user interface, the pair of infection samples identified as being a potential transmission within a phylogenic tree of sequenced infection samples.

11. The system of claim 10, wherein the configured processor determines the expected range of changes by:
building a phylogeny of sequenced samples to identify closely-related samples
computing, for at least one of the plurality of infection samples, the number of changes over time between the sample and at least one closely-related sample as determined by the phylogeny.

12. The system of claim 11, wherein the configured processor builds the phylogeny by computing pairwise distances between each pair of sequenced samples and using a distance matrix to build a phylogenic tree.

13. The system of claim 10, wherein the configured processor determines an expected rate of changes over time for a pathogenic organism using linear regression on sample data which contains changes over time for different samples and computing a prediction interval.

14. The system of claim 12 wherein the processor is further configured to:
determine which of said infection samples are from the same outbreak by conducting a breadth first search on the phylogenetic tree of the samples traversing edges with a number of changes within the expected range of changes.

* * * * *